United States Patent [19]
Liu

[11] Patent Number: 6,159,749
[45] Date of Patent: Dec. 12, 2000

[54] HIGHLY SENSITIVE BEAD-BASED MULTI-ANALYTE ASSAY SYSTEM USING OPTICAL TWEEZERS

[75] Inventor: Yagang Liu, Irvine, Calif.

[73] Assignee: Beckman Coulter, Inc., Fullerton, Calif.

[21] Appl. No.: 09/119,837

[22] Filed: Jul. 21, 1998

[51] Int. Cl.[7] .................. G01N 33/552; G01N 33/543; G01N 33/53; F21V 9/16; G01R 9/02

[52] U.S. Cl. .................. 436/527; 435/7.1; 435/7.93; 435/7.94; 435/174; 436/172; 436/174; 436/518; 436/527; 436/524; 436/528; 436/529; 436/533; 436/534; 436/543; 436/544; 436/545; 436/546; 250/251; 250/458.1; 250/459.1; 356/346

[58] Field of Search .................. 435/7.1, 7.93, 435/7.94, 174; 436/172, 174, 518, 527, 524, 528, 529, 533, 534, 543, 544, 545, 547, 546; 422/82.05, 82.08, 82.09, 811; 250/251, 458.1, 459.11; 356/346

[56] References Cited

U.S. PATENT DOCUMENTS

| | | | |
|---|---|---|---|
| 4,893,886 | 1/1990 | Ashkin et al. | 350/1.1 |
| 5,512,745 | 4/1996 | Finer et al. | 250/251 |
| 5,620,857 | 4/1997 | Weetall et al. | 435/7.1 |
| 5,736,410 | 6/1995 | Zarling et al. | 436/172 |

OTHER PUBLICATIONS

Schutze et al., Catch and Move, Nature 368: 667–669 (Apr. 14, 1994).

Buican et al., Automated single cell manipulation and sorting by light trapping, Applied Optics 26(24): 5311–5316 (Aug. 1, 1987).

*Primary Examiner*—James C. Housel
*Assistant Examiner*—Gailene Rio Gabel
*Attorney, Agent, or Firm*—William H. May; Margaret A. Kivinski

[57] ABSTRACT

An apparatus and method for chemical and biological analysis, the apparatus having an optical trapping means to manipulate the reaction substrate, and a measurement means. The optical trapping means is essentially a laser source capable of emitting a beam of suitable wavelength (e.g., Nd:YAG laser). The beam impinges upon a dielectric microparticle (e.g., a 5 micron polystyrene bead which serves as a reaction substrate), and the bead is thus confined at the focus of the laser beam by a radial component of the gradient force. Once "trapped," the bead can be moved, either by moving the beam focus, or by moving the reaction chamber. In this manner, the bead can be transferred among separate reaction wells connected by microchannels to permit reactions with the reagent affixed to the bead, and the reagents contained in the individual wells.

16 Claims, 4 Drawing Sheets

FIG. 1
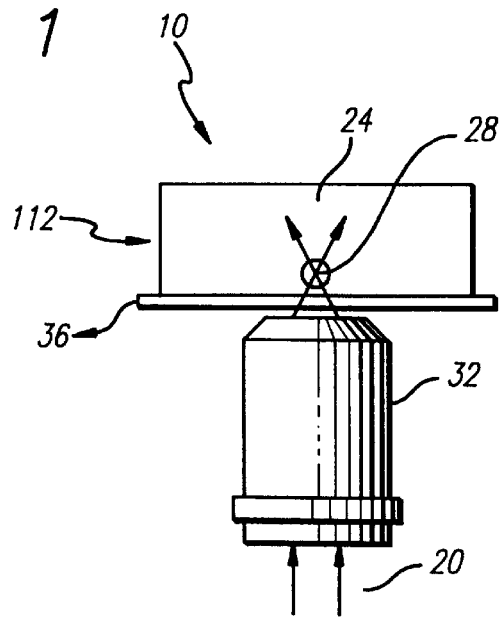
FIG. 2A
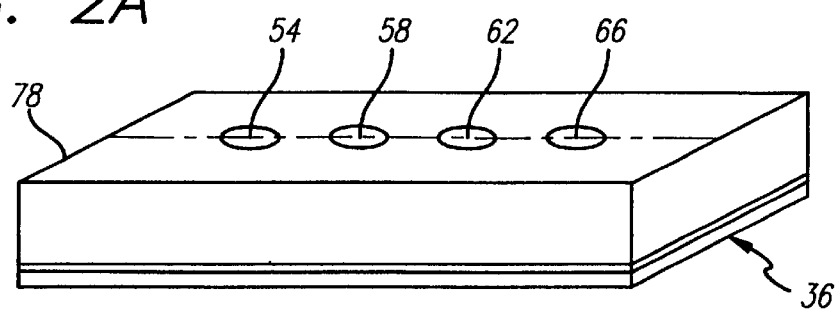
FIG. 2B
FIG. 2C
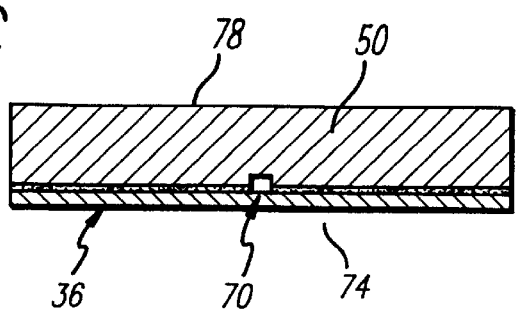

HIGHLY SENSITIVE BEAD-BASED MULTI-ANALYTE ASSAY SYSTEM USING OPTICAL TWEEZERS

BACKGROUND OF THE INVENTION

1. Field of the Invention

This invention relates to identification of components in a biological or chemical sample by optical trapping means.

2. Description of Related Art

Numerous instruments, kits and methods generally related to the identification and quantitation of chemical and biochemical moieties are currently available. At present, none of these rely on an "optical trapping means" or "optical tweezers" as described herein, to manipulate the reaction substrate for the purpose of controlling the reaction, and for the purpose of obtaining accurate measurement using only a small sample size. The optical trapping means consists essentially of a laser capable of emitting a beam of suitable wavelength (e.g., Nd:YAG laser). The beam impinges upon a microparticle (e.g., a 5 micron polystyrene bead which serves as a reaction substrate), and the bead is thus confined at the focus of the laser beam by a radial component of the gradient force. Once "trapped" the bead can be moved, either by moving the beam focus, or by moving the reaction chamber. In this manner, the bead can be transferred among separate reaction wells, to permit reaction between the reagent affixed to the bead, and the reagent contained in that well.

This optical trapping means has been previously characterized in the art and is the subject of U.S. Pat. No. 4,893,886 to Ashkin, Non-destructive optical trapping means for biological particles and method of doing same, assigned to AT&T, and issued on Jan. 16, 1990.

The apparatus, method, and system of the present invention is suitable for a variety of applications: chemistry, biochemistry, immunology, etc. Applications for which the present invention are presently suited are immunological assays ("immunoassay"). Such techniques are directed to, for example, probing antigen-antibody interactions.

Briefly, an antibody is a molecule produced by the immune system of an animal in response to a foreign particle or pathogen (e.g., a disease-causing bacterium). The antibody is able to recognize (chemically bond to) a particular portion of the foreign particle known as the antigen; a single foreign particle may have several antigens, though a particular antibody binds to only one of them. This recognition and subsequent binding are among the initial stages in the immune response. Hence, specific antibodies are produced by the body in response to particular pathogens. And therefore, the presence of a particular antibody in the blood is a reliable indicator of a particular infection, which may be found long before the onset of any signs or symptoms of the disease. Indeed, since at a given moment, antibody levels may far exceed the pathogen levels in the body, it is far easier to look for the presence of the antibody—as an indicator of the disease—than it is to look for the pathogen directly. Consequently, one common technique for determining whether a person is infected with a disease-causing pathogen is to assay for the presence of particular antibodies.

In addition, antibodies form very strong chemical bonds with a particular antigen found on the surface of the pathogen. Thus, particular antigens can be isolated, and used as "probes," in the following manner. A small sample of blood is taken from a person; the antigen probe is then added to the sample. If the blood sample contains antibody specific for that antigen, then it will chemically bind to the antigen probe. Finally, the investigator needs a means to determine whether this binding has occurred. This can be done in a variety of ways. Perhaps the simplest way relies upon the fact that an antigen-antibody complex will precipitate out of solution (i.e., form a solid and settle out of the solution) allowing it to be easily identified, even by visual inspection. Again, numerous immunological techniques are currently available either commercially or described in the scientific literature. A concise review of these techniques is provided in *Immunolog*, Roitt, et al. eds. (1996), which is hereby incorporated by reference into the present Application. The simplest such method—just discussed—is probably the precipitin reaction, which exploits the tendency of antigen-antibody complexes to precipitate from solution when combined in proportions at or near equivalence. Hemagglutination and complement fixation describe more sophisticated techniques, which allow antibody to be detected and measured at far lower concentrations than those detectable by the method just discussed; these methods can readily detect antibody at levels of less than 1 $\mu$g/ml. Direct and indirect immunofluorescence relies upon fluoresceinated antibody which, when exposed to UV light, will fluoresce green if bound with antigen. Immunoassay techniques rely on labeled reagents (e.g., fluorescent, chemiluminescent, or radioisotope markers) for detecting antigens and antibodies, and include both solid-phase assays (one reagent fixed to a solid support) and ELISA (enzyme-linked immunoabsorbent assay). One such system is described in U.S. Pat. No. 4,623,629, *Solid-phase immunoassay support and method of use thereof*, issued to Daniel Kerschensteiner. Magnetic beads can be moved by forces of a magnetic field, these forces typically are not confined to a single bead.

Current analytical techniques are generally plagued by the following problems: (1) the sample size is too small to reliably identify the sought-after substance; and (2) the technique is too slow and/or is not amenable to automation. The apparatus and method of the present invention addresses these problems in the following way. One, the reaction substrate is a single micron-sized bead; moreover, the detection method is in constant coincidence with the bead location, which is fixed by the optical trapping means, hence the measurement is highly sensitive and easily automated. Second, because the bead is readily transferred from one reservoir to another, measurement can take place in a "clean" reservoir, free of background reagents, which allows more accurate measurement. Finally, random access to bead (s) on which different chemical are coated, can enable multianalyte analysis.

SUMMARY OF THE INVENTION

One object of the present invention is to provide an apparatus for performing a series of chemical, biological, or immunological reactions.

An additional object of the present invention is to provide a method for performing a chemical, biological, or immunological assay.

Another object of the present invention is to provide a method for performing a non-competitive immunoassay for detection of a compound of interest in a biological sample.

An additional object of the present invention is to provide a method for performing a competitive immunoassay for detection of a compound of interest in a biological sample.

Thus, in accomplishing the foregoing objectives, there is provided in accordance with one aspect of the present invention, an apparatus for performing a series of chemical biochemical, or immunological reactions comprising a reaction chamber having a plurality of reaction wells, connected by a microchannel; an optical tweezer, for trapping a particle in a well; a movement means for transferring said trapped particle to another said well, through said microchannel; and a detection means for detecting reactions on said particle.

In one preferred embodiment of the present invention, the detection means referred to above is a fluorescence detector.

In another preferred embodiment of the present invention, the detection means referred to above is a fluorescence detector and is in coincidence with said optical trapping means.

In still another preferred embodiment of the present invention, the reaction chamber referred to above is mounted on a motion stage.

In accordance with another aspect of the present invention, there is provided an apparatus for performing a series of immunological reactions comprising: a reaction chamber having a plurality of reaction wells, connected by a microchannel; an optical tweezer created by a laser beam emitted by a Nd:YAG laser or other laser source, for trapping a particle in a well; a motion stage upon which said reaction chamber is mounted, for moving said chamber, thus transferring said trapped particle from one well to another, through said microchannel; a means for receiving information regarding the position of said particle relative to said reaction well, and for responding to said information by altering the movement of said motion stage; and a fluorescence detector comprising an excitation laser diode and a photon counter, for detecting reactions on said particle, said detector in coincidence with said laser beam.

In accordance with yet another aspect of the present invention, there is provided a method for performing a chemical biological, or immunological assay comprising the steps of: loading microbeads into a first well, loading a reagent into a second well; transferring, by optical tweezer means, a microbead from said first well into said second well; and identifying the presence, or measuring the quantity of said reagent on said microbead.

In accordance with a further aspect of the present invention, there is provided a method for performing a non-competitive immunoassay for detection of a compound of interest in a biological sample comprising the steps of: loading microbeads coated with capture antibodies into a first well, loading a biological sample to be tested for the compound of interest into a second well, loading labeled antibodies into a third well, and loading buffer into a fourth well; transferring, by optical tweezer means, a microbead from said first well into said second well, through a microchannel connecting said wells, allowing sufficient time for said microbead to bind the compound of interest, if it is present in the biological sample; transferring, by optical trapping means, said microbead from said second well into said third well, through a microchannel connecting said wells, allowing sufficient time for said labeled antibodies to bind said microbead if the compound of interest is bound to said microbead; transferring, by optical trapping means, said microbead from said third well into said fourth well through a microchannel connecting said wells; and measuring the quantity of said label to the concentration of the compound of interest.

In accordance with still another aspect of the present invention, there is provided a method for performing a competitive immunoassay for detection of a compound of interest in a biological sample comprising the steps of: loading microbeads coated with labeled antibody into a first well, loading a sample and labeled antigen into a second well, and loading buffer into a third well; transferring, by optical tweezer means, a microbead from said first well into said second well, through a microchannel connecting said wells, allowing sufficient time for said microbead to bind an antigen of interest, if it is present in the biological sample; and measuring the quantity of antigen of interest bound to said microbead.

Other and further objects, features, and advantages will be apparent in the following description of preferred embodiments of the invention, given for the purpose of disclosure and taken in conjunction with the accompanying drawings.

BRIEF DESCRIPTION OF THE DRAWINGS

The invention will be more readily understood by review of the specification in light of the following accompanying drawings, depicting examples of preferred embodiments of the invention.

FIG. 1 is a cross-sectional view showing the key components of an optical trapping device at the point where the laser beam impinges upon the bead.

FIG. 2 is oblique (FIG. 2a) and cross-sectional (FIG. 2b, FIG. 2c) views showing a multi-well reaction chamber which holds the reagents and allows the optical trapping device to transfer microbeads from one well to another.

Figure 3:
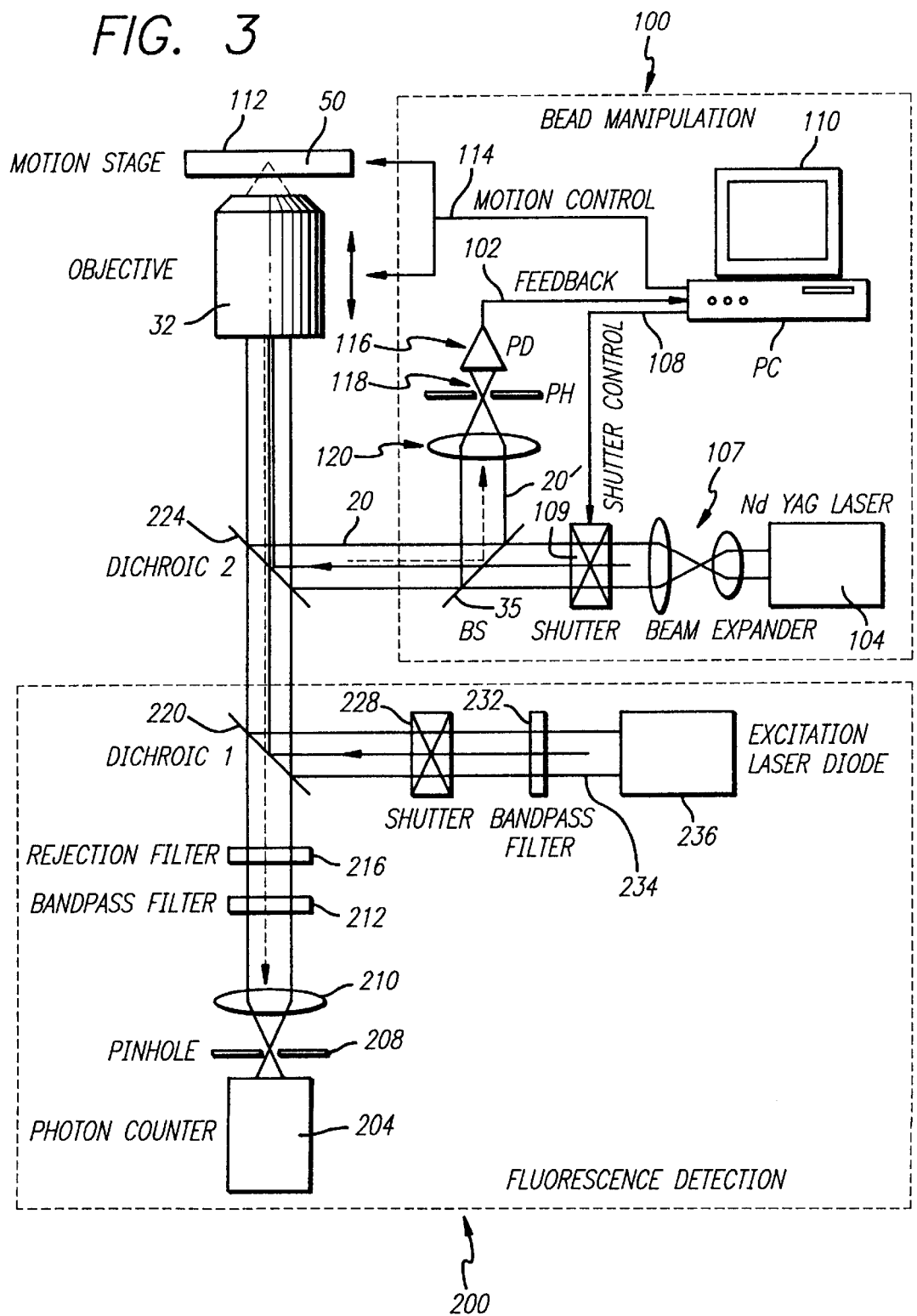
FIG. 3 is a schematic diagram of an entire system embodying the present invention; essentially two sets of components are shown: those relating to bead manipulation, and those for fluorescence detection.

The drawings and figures are not necessarily to scale; certain features of the invention may be exaggerated in scale or shown in schematic form in the interest of clarity and conciseness.

DETAILED DESCRIPTION OF THE PREFERRED EMBODIMENTS

The skilled artisan will quickly realize that various substitutions and modifications may be made to the invention disclosed herein without departing from the scope and spirit of the invention.

One preferred embodiment of the present invention will now be described, in accordance with FIGS. 1–3. The primary components of the apparatus of the present invention are the optical trapping means and the multi-well reaction chamber. The optical trapping device captures the particle from solution, moves it from one reaction well to another to allow it to contact different reagents, and finally, holds it for detection (measurement of the concentration of certain reagents bound to the bead after reaction). The reaction chamber consists of a series of individual reaction wells which hold the reagents, and are connected by a microchannel to allow the microbead to be actively transferred from one well to another.

The optical trapping means is essentially the type described in the Ashkin patent ('886) which is a single-beam gradient force trap. According to the '886 patent, this force trap consists of a strongly focused laser beam which has a near Gaussian transverse intensity profile. The stabilizing effect on the trapped particle arises due to the combination of the radiation pressure scattering and gradient force components which combine to give a locus of stable equilibrium near the focus of the laser beam. Thus, stabilizing the trapped particle occurs by strongly focusing the laser beam such region. Once the particle is trapped, this method can also be used, as it is in the methods and apparatus of the present invention, for transferring the particles from one location to another, as well as for suspending it for measurement.

FIG. 1 depicts the essential features of the optical trapping means. Thus, the optical trapping means 10 of the present invention captures, holds, and transfers a selected particle by a three-dimensional restrictive force. This force is ideally suited to hold microsized dielectric particles at its beam focus in a liquid medium. An incident laser beam 20, from a source not shown, is aimed generally in the direction of the liquid solution 24 held in the individual wells comprising the reaction chamber. A laser beam of suitable wavelength should have an emission band that is well separated from the excitation and emission bands of the dyes to be detected. Generally, a near-infrared laser is preferred (>650 nm). The laser beam 20 enters a microscope objective 32 and passes through a microscope cover glass 36 until it reaches the microbead 28. In a preferred embodiment the laser beam 20 is emitted by a Nd:YAG laser. According to one particularly preferred embodiment, an effective optical trapping means suitable to execute the purposes of the present invention can be created by using a high numerical aperture (numerical aperture, or N.A, equal to about 1.2 to about 1.4) microscope objective lens 32 to focus a laser beam 20 through the solution to capture the particle 28. Hence, a dielectric particle 28 (i.e., the microbead) near the beam focus is pulled into and held stable in the trap created by the beam 20. The trapped particle 28 can then be transferred from one reaction vessel within the reaction chamber to another simply by shifting the beam focus, since the particle will move according to the beam focus. In preferred embodiments, the particle 28 is held by the beam 20, and transferred among different reaction wells within the chamber by movement of the entire chamber; thus the beam focus (and the particle trapped within the beam) remain fixed during reaction and detection.

The optical trapping means is preferably mounted below the reaction chamber, such that the laser beam 20 is directed upward through the objective lens 32, and into the solution where the particle resides. Preferably the laser source (not shown) and the microscope objective remain fixed in place; the particle is transferred by movement of the reaction chamber, which is mounted on a moveable stage.

The second crucial component of the apparatus of the present invention is the multi-well chamber 50, depicted in FIG. 2. The individual wells (or reaction vessels) comprising the chamber are shown at 54, 58, 62, or 66. Each well is connected by at least one other well by a microchannel 70, which traverses the length of the reaction chamber along the bottom of the individual wells. The skilled artisan will immediately recognize that this configuration is not crucial to the invention.

The microchannel permits the active transfer (by optical trapping means) of a microbead 28 from one well 54, 58, 62 or 66 to another within the multi-well chamber 50. Ideally, the microchannel is effectively impermeable to the passive diffusion of the reagents contained in the reaction wells 54, 58, 62 and 66. Indeed, the microchannel is intended to be impermeable to all microbeads other than the one under active control by the laser beam 20. To achieve this, the microchannel 70 should preferably have a very small cross-sectional diameter. For example, in one preferred embodiment, a microchannel having a cross-sectional diameter of $10 \times 10$ $\mu m^2$ was found to be sufficient to allow the active movement of a 5-$\mu$m microbead, yet still restrict the movement of other microbeads and other reagents into the microchannel 70. The skilled artisan will wish to manipulate the design of the microchannel 70 to achieve the tolerable level of unwanted diffusion; for example, the cross-sectional diameter can be varied, as well as the length of the channel (i.e., the distance between the wells 54, 58, 62 and 66).

The bottom 74 of the multi-well chamber 50 is covered with a sub-millimeter to about ten millimeters thick microscope cover glass of microscope-grade quality, or another suitable material. The particular type of glass is dictated by the microscope objective lens used in the apparatus. An appropriate type will be readily apparent to the skilled artisan, depending upon the experimental protocol. Finally, the sides and top portion 78 of the multi-well chamber 50 are preferably constructed of glass or rubber or other chemical resistance materials.

Having described in detail the optical trapping means and the reaction well chamber, the entire "system" of the present invention, according to one preferred embodiment, will now be described. FIG. 3 depicts the system, comprised of two primary sets of components: those relating to microbead manipulation 100, and those relating to fluorescence detection 200.

The optical trapping means is created by directing a beam 20 from a suitable source. In one particularly preferred embodiment, the source is a Nd:YAG laser 104 (though virtually any laser source capable of generating a beam of suitable wavelength would suffice). The beam 20 is directed to a high N.A. microscope objective 32, where it is directed upon the multi-well chamber 50, which is mounted on a motion stage 112. A microbead 28 is trapped or released (i.e., the laser is turned on or off) by opening or closing a shutter mechanism comprised a first shutter 109 and a shutter control 108. Hence, in this preferred embodiment, a beam 20 is emitted from a Nd:YAG laser 104, passes through a beam expander 107, after which it is directed through the objective 32 by a second dichroic mirror 224 and onto the solution in the multi-well chamber 50. The beam 20 can be deactivated by manipulating the first shutter 109, by means of a shutter control 108.

The upper portion 100 of FIG. 3 shows how a feedback signal 102 may be generated from the backscattered radiation 20'. In particular, any backscattered radiation is returned via the objective 32, second dichroic mirror 224 (which reflects only the radiation wavelengths emitted from the Nd:YAG laser 104), beam splitter 35 (which preferably also blocks the backscattered light 20' from being transmitted back to the Nd:YAG laser 104), first pinhole 118 and lens 120. The power and location of lens 120 and pinhole 118 relative to the photodiode 116 is such that the photodiode 116 is illuminated only by collimated radiation from the objective 32, i.e., radiation that originates at the focus of the objective 32. Accordingly, the amplitude of the feedback signal from photodiode 116 will be indicative (after comparison with previously calibrated backscattering data stored in personal computer 110) of the optical properties (backscattering) of whatever is present at the focus. In particular, it will indicate whether the objective 32 is focused on the top or bottom surface of the microscope coverglass 36, on the liquid solution 24 inside the wells 54, 58, 62 or 66 and microchannels 70, or on a microbead 28 optically trapped by the laser beam 20, since each will have somewhat different backscattering properties at the wavelength in question. Thus the feedback signal can be used during a preliminary "scan and trap" operation to determine whether any microbead 28 has yet been trapped at the focus, and if so, to determine its approximate diameter (if more than one size of microbead is present). Once a microbead 28 of the desired size is suspended at the focus, the desired analytical process may be performed, including the micromanipulation of the microbead 28 in the different wells 54, 58, 62 and 66 via motion control signal 114, and the detection of any resultant fluorescence by the detection subsystem (lower portion 200 of FIG. 3). Those skilled in the art will realize that the feedback signal 102 could also be used to position the motion stage at a predetermined position relative to the objective prior to the trapping of any microbead. After the desired microbead has already been trapped, the feedback signal 102 can also cause any movement of the motion stage 112, to be halted and/or reversed before the microbead has been dislodged from the optical trap, e.g., by forcible contact with the floor or a wall of the wells 54, 58, 62, 66 or with another surface. However, as currently contemplated, conventional open loop positioning techniques (e.g., precision molding or machining of registration surfaces, programming a stepper motor with predetermined position and velocity profiles) are expected to be sufficient to keep the trapping beam and microbead centered between the two side walls of the microchannel 70 without any detectable change in the feedback signal 102 from the photodiode 116, before the microbead has been substantially displaced from the focus of the trapping beam and before a substantial portion of the trapping beam 20 has been backscattered by the inert material defining the microchannels 70.

The detection portion 200 of the system will now be described. The purpose of this portion of the system is to identify/quantify the reagents that reacted with those on the microbead's surface. The skilled artisan will immediately recognize that numerous detection techniques are suitable in conjunction with the present invention. The embodiment described in FIG. 3 incorporates a fluorescence detection method. One key aspect of this preferred embodiment is, as evidenced by FIG. 3, that the detection beam 234 is automatically locked onto the optically trapped bead 28. Thus, the detection beam 234 and the laser beam 20 are designed so that they are directed through the objective 32 coaxially; moreover, this coincidence remains throughout the assay since neither the trapping beam 20 nor detection beam 234 moves; instead what is moved is the motion stage 112, which houses the multi-well chamber 50. Both the trapping and detection beams are directed through the objective at all times. Therefore, repeated focusing and searching is eliminated in this preferred embodiment.

The excitation light or detection beam 234 (from, e.g., laser diode 236 or other light source) is directed at the target (i.e., the microbead) by a first dichroic mirror 220. The fluorescence from the bead is collected by the same objective lens 32 and directed to the photon detector 204 (i.e., photon counter) for measurement.

Other preferred features of the detection apparatus include: second pinhole 208, second lens 210, second bandpass filter 212, rejection filter 216, first dichroic mirror 220, second dichroic mirror 224, second shutter 228, first bandpass filter 232, and excitation laser diode 236. The excitation laser diode 236 directs a beam through the objective 32 and onto the microbead 28 (upon which the objective is already focused) and the resulting fluorescence is received by the photon counter 204.

The principal advantages of the present invention derive largely from the optical trapping means, which is ideally suited for: (1) isolating a single microbead of submicron (or larger) size; (2) transferring the microbead from one reaction vessel to another via a system of microchannels which connect the reaction vessels; (3) suspending the microbead in the presence of a particular reagent, to allow the desired reaction (or measurement) to occur; and (4) performing confocal microscopic detection from the trapped bead since the trapped bead is located at a focal position, the detection system is automatically focused. Such an apparatus and method possess the following attributes not generally found in state-of-the-art systems.

First, because the total binding sites on the microbeads are well known, the reactions (which occur on the surface of the beads) are well controlled. This is an essential attribute of a high sensitivity "microspot" immunoassay.

Second, because the area of the microbead is only on the order of tens of square microns, the analysis can be performed using very small quantities of sample and antibody/reagent (e.g., microliter or less).

Third, after the desired reactions (e.g., antigen-antibody) occur, the affinity (or extent of reaction) must be measured. The efficacy of any such apparatus or method is necessarily limited by this final detection step. One factor which confounds accurate measurement is the presence of background reagents, or "chemical cross interference." In the present invention, this factor can be essentially eliminated since different reagents are placed in different reaction vessels. Thus, the measurement can be performed in a well separate from the one in which the reaction(s) occurred, because the microbead is easily transferred from a reaction vessel to a separate well for measurement. In addition, detection sensitivity is improved by: (1) confocal measurement; (2) high efficiency of fluorescence collection (due to the high numerical aperture of the objective lens used), and (3) the ability to hold a target bead at a focal position for as long as needed. The improved detection sensitivity enables single molecular detection.

Fourth, another factor that confounds accurate measurement is the final "wash step," which is normally performed immediately prior to measurement for the purpose of removing excess (unbound) reagents, background ions, etc., from the microbeads. This process is unfortunately somewhat nonselective: removal of unbound reagent also removes some bound reagent. Thus, one unintended—but unavoidable—effect of this step is the removal of the desired or bound analyte from the microbead, thus resulting in a lower measurement. In the present invention, this washing step is avoided since the microbead can simply be transferred into a separate well for measurement. Put another way, the wash step is automatically performed upon transferring the microbead from one well to another. Hence, the washing step is not technically eliminated, but is simply not required as a separate step in the method, requiring separate components to the apparatus.

Fifth, the apparatus of the present invention is comprised of a reaction chamber, in turn comprised of a series of reaction vessels or wells. Again, the contents of each well is nontransferable to another well, except that a microbead placed in one well can be moved by optical trapping means, through tiny microchannels that connect the wells. These independent wells, each one containing a separate reagent, naturally allow superior multianalyte, and random access capabilities, which means that numerous independent assays can be performed on a single sample of limited quantity (e.g., microliter).

Sixth—though the apparatus and method of the present invention are not limited to fluorescence detection—if this technique is used, it has the following attributes not available in state-of-the-art instruments/methods: (1) the detection focus will not be missed because the beam produced by the optical trapping device is capable of holding the microbead at the exact focal position of the measuring device (i.e., the detection instrument is automatically locked onto the trapped bead, hence no complicated microspot searching and focusing procedure is required as with other methods); (2) the fluorescence collection efficiency from the microbead is unusually high since one embodiment of the present invention is comprised of a microscope objective having a very high numerical aperture (N.A=1.3 or 1.4); and (3) the confocal detection with high spatial resolution can efficiently eliminate the fluorescence and scatter background from the surroundings. This latter attribute results in high photon collection efficiency from a microsized spot. Moreover, this latter attribute eliminates linear and nonlinear scatter background.

In combination, the above attributes of the present invention result in an apparatus and method that is superior to the state-of-the-art. In summary, the present invention allows more accurate measurement of more analytes using less sample, and at lower cost. In addition, the present invention is extraordinarily easy to practice. The crucial steps involve: trapping the microbead, transferring the bead among the different wells, and holding the bead to allow the desired reaction/measurement to occur. In addition, measurement is greatly simplified because the optical trapping means holds the microbead precisely at the detection locus. That is, the beam produced by the optical trapping device is in deliberate coincidence with the detection beam. Moreover, the method of the present invention can be readily automated; only a motion stage is required. Finally, the entire apparatus can be constructed so that it is very compact, relative to currently available instruments of similar utility.

EXAMPLE 1

Simple Immunoassay

The simplest possible embodiment of the invention can be described as follows: For the purposes of this description, the desired assay is an immunological assay. This apparatus would consist of a reaction chamber in turn consisting of two wells connected by a microchannel. This microchannel would allow only the microbeads to pass from the first well into the second well by the means of optical tweezers. It would not permit the exchange of other reagents between the two wells. The first well would contain the microbeads, preferably constructed of either glass or polystyrene, and from about 0.1 micron to about 20 microns in diameter. The microbeads would be coated with the desired reagent; for example, a capture antibody. The second well would contain the sample which may contain an analyte of interest; for example, human serum. The sample is preferably, though not exclusively, a biological sample (blood, serum, urine, semen, or any other natural exudate, or biological fluid). The amount of sample can be very low, e.g., in the microliter range. The second well also contains a labeled probe, for example a fluorescent antibody. In the simplest embodiment, the desired measurement would also occur in this second well, provided that the contribution from free probes is minimized by confocal detection. Alternatively, or the detection method can be fluorescence polarization in a homogenized format. In other more complex embodiments, the measurement would occur in a separate well. A variety of detection methods can be incorporated into the apparatus of the present invention; for example, fluorescence. Detection sensitivities of the present invention are single molecular.

Hence, the simplest apparatus of the present invention would consist of two wells for holding the reagents, a microchannel joining the two wells and which allows only microbeads to pass—but not other reagents, microbeads to which a reagent(s) is affixed and which can be isolated and manipulated by an optical trapping means, and finally a detection means for measuring reactivity/affinity. In the simplest possible embodiment, the detection means is located in the second well so that it can measure the desired parameter in situ.

The simplest method of the present invention can be described in this manner. Using the apparatus described in the previous paragraph, the first well is loaded with, for example, microbeads coated with antibody. The second well contains the analyte sample; for example, human serum. One microbead is isolated using the optical trapping means referred to above; the microbead is then transferred via the microchannel into the second well. The antibody-coated microbead is allowed to react with the antigens contained in the serum sample. In this simplest method, the affinity of the serum antigen for the capture antibody can be measured in situ, i.e., in the second reaction well.

EXAMPLE 2

One Preferred Reaction-Well Chamber Design

In this preferred embodiment, a microchannel having a cross-sectional diameter of 10×10 $\mu m^2$ was found to be sufficient to allow the active movement of a 5-$\mu$m microbead, yet still restrict the movement of other microbeads and other reagents into the microchannel. This apparatus was constructed with a microchannel having a length of 2 mm, which was found to effectively curtail molecular diffusion of molecules having a diffusion coefficient of $10^{-10}$ $m^2/s$, for 5.5 hours, and for microbeads, diffusion was inhibited nearly infinitely. The bottom of the well and channel should be a microscope cover glass whose thickness is from 100 $\mu$m to 200 $\mu$m. The optical trapping means was capable of transferring a 5 $\mu$m bead between two contiguous wells—under the above parameters—in only a few seconds. Therefore, over a several hours' span, the wells can be isolated except for the selected microbead trapped by the optical trapping means.

EXAMPLE 3

Non-Competitive "Sandwich" Immunoassay Technique

A method for identifying antibodies or measuring antigen-antibody interactions that embodies the present invention will now be demonstrated. The reaction well and microbead parameters are as depicted in the previous example. This technique preferably is performed using the system described in the Detailed Description above.

Figure 4:
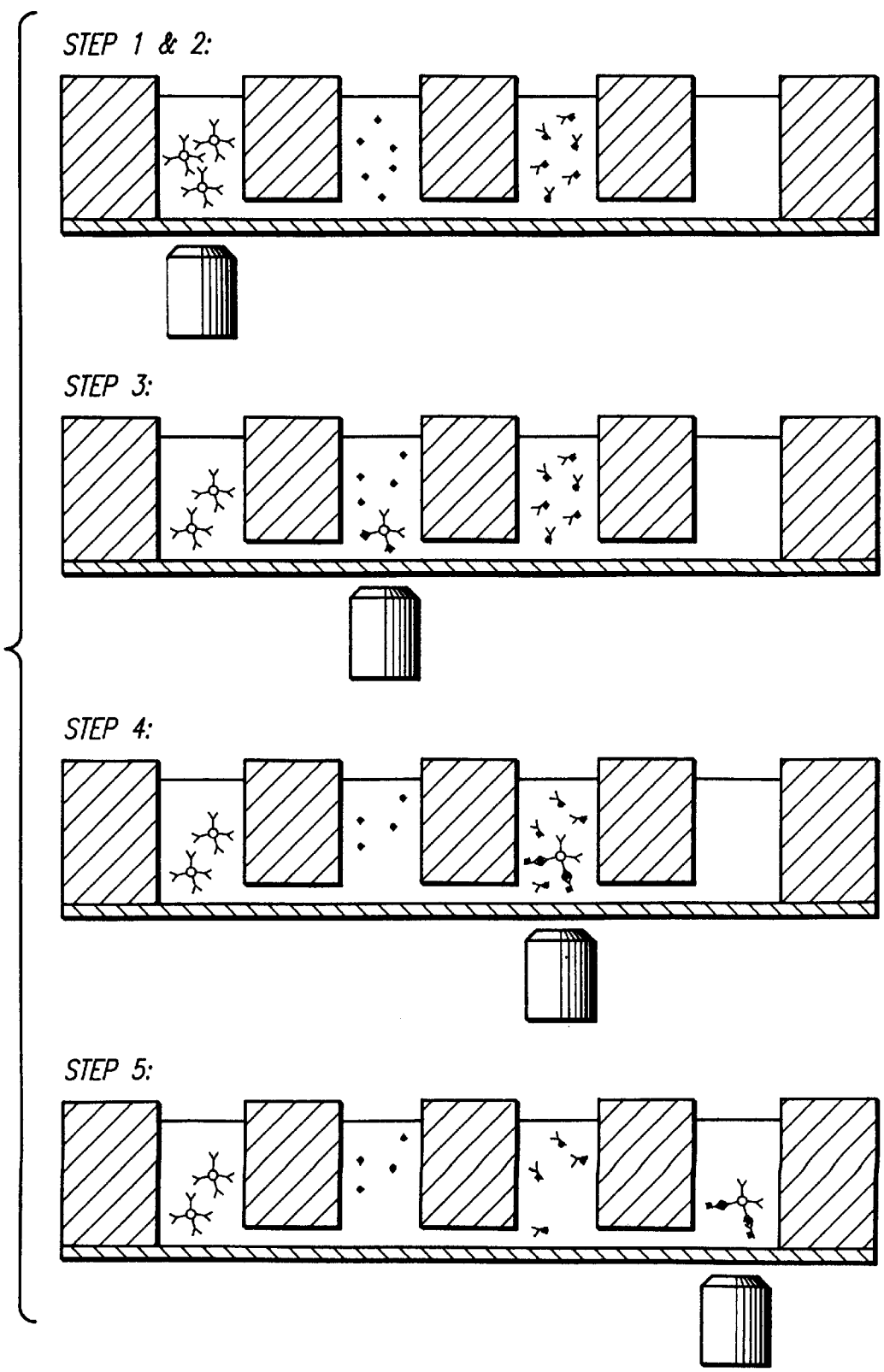
FIG. 4 depicts a cross-section of a reaction well chamber of the present invention; the individual wells, as well as the microchannel joining the wells are shown. Multiple chambers are shown to depict the actual sequence of steps involved in performing a method of the present invention

FIG. 4 depicts a cross-section of a reaction well chamber of the present invention; the individual wells, as well as the microchannel joining the wells, are shown. Microbeads coated with "capture antibodies" are loaded into the first well (shown as the left-most well comprising the reaction chamber); serum sample is loaded into well 2; labeled antibody is loaded into well 3; and clear buffer solution is loaded into well 4, thus completing step 1. In step 2, the optical trapping means fixes a microbead in place by turning on the trapping laser and capturing a bead in well 1. In step 3, the entire reaction well is shifted such that the trapped microbead passes from the first well into the second well through the microchannel. In well 2, the capture antibodies affixed to the microbead bind antigen present in the serum sample. Next, the microbead is transferred into well 3, where the captured antigen reacts with labeled antibody (step 4). In step 5, the microbead is transferred from well 3 into well 4, where it undergoes fluorescence detection for the presence of labeled antibody.

EXAMPLE 4

Competitive Immunoassay Technique

A second method for identifying antibodies or measuring antigen-antibody interactions that embodies the present invention will now be demonstrated. The reaction-well and microbead parameters are as depicted in the previous example. This technique preferably is performed using the system described in the Detailed Description above.

Figure 5:
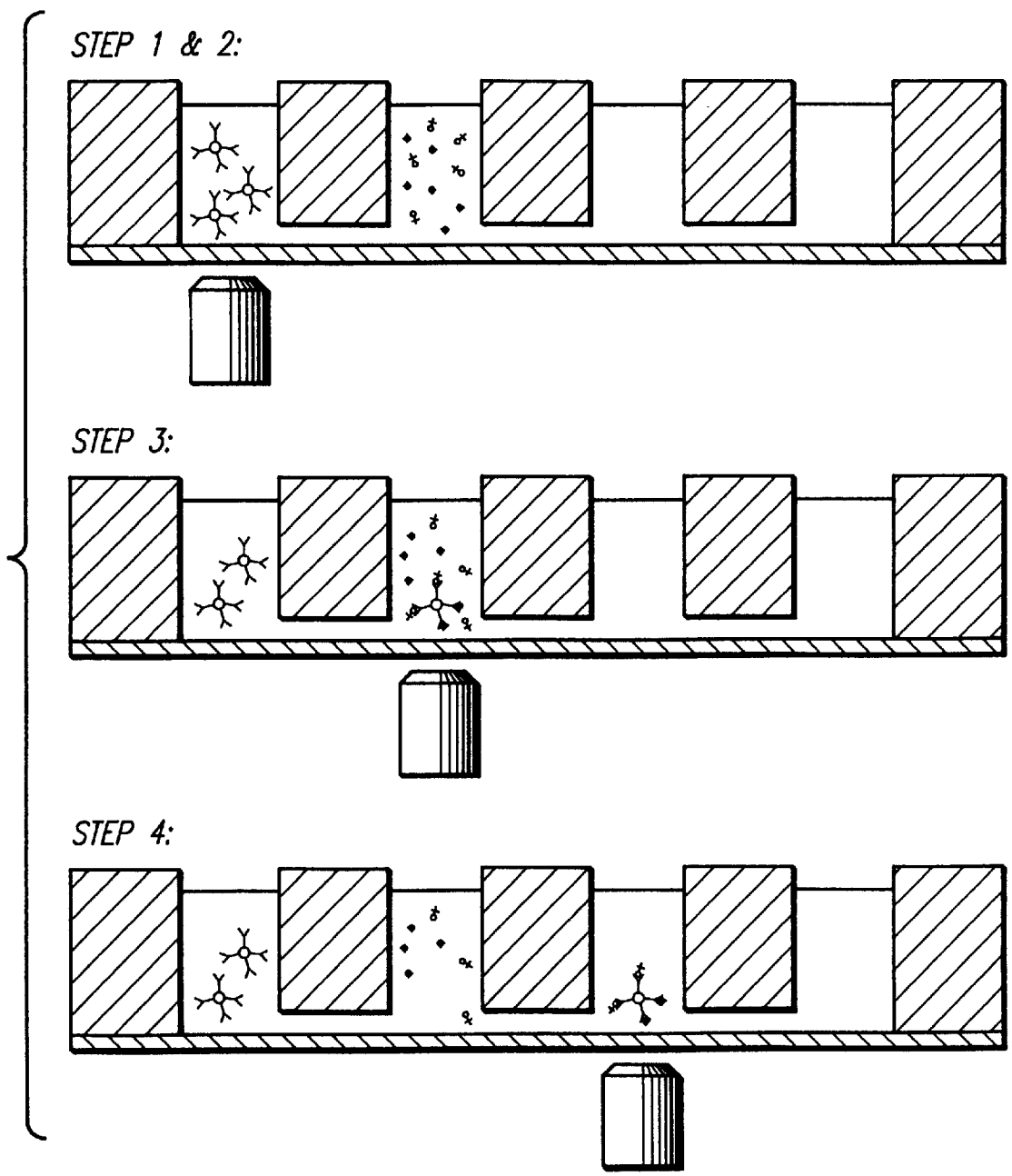
FIG. 5 depicts a cross-section of another reaction well chamber of the present invention; the individual wells, as well as the microchannel joining the wells are shown. Multiple chambers are shown to depict the actual sequence of steps involved in performing a method of the present invention.

FIG. 5 depicts a cross-section of another reaction well chamber of the present invention; the individual wells, as well as the microchannel joining the wells, are shown. Microbeads coated with antibody are loaded into the first reaction well (shown as the left-most well comprising the reaction chamber). This is step 1 as shown in FIG. 5. Into the second well are loaded the sample (e.g., serum) and labeled antigen. Into the third well is a buffer to facilitate detection.

The second step in the method consists of trapping a bead by an optical trapping means, for example by turning on the trapping laser and capturing a bead in well 1.

The third step in the method consists of moving the trapped bead through the microchannel to the second well. In this second well, the antibody-coated bead reacts with antigen present in the serum sample. Antigen in the sample competes with labeled antigen. The measurement of labeled antigen bound to the antibody can be performed in the second well (provided background can be minimized or the detection method can be polarization in a homogeneous format), or in a separate, third well. In the latter case, the microbead is transferred via another microchannel joining the second and third wells (step 4). Throughout the movement of the microbead from initial isolation in the first well until measurement in the last well, the laser beam remains fixed upon the microbead—i.e., throughout the method, the bead remains fixed in place, though the entire reaction well chamber is moved, allowing the bead to be transferred from one well to another through the microchannel.

The skilled artisan will readily appreciate that the present invention is well adapted to carry out the objects and to obtain the ends and advantages mentioned, as well as those inherent in the invention. The methods, apparatus, assays, procedures, techniques, and equipment described herein are representative of the preferred embodiments, are intended to be exemplary and not intended as limitations on the invention scope. Additional embodiment of the invention not described herein but within the spirit of the invention, will occur to the skilled artisan, yet are fully encompassed by the scope of the claims.

What is claimed is:

1. A method for performing an assay for detecting an analyte contained in a sample, comprising the steps of:

(a) providing a microbead coated with an anti-analyte reagent that recognizes and binds to the analyte;

(b) providing a labeling reagent that recognizes and binds to the analyte;

(c) loading the microbead into a first well, loading the sample and the labeling reagent into a second well;

(d) transferring, by optical trapping means, the microbead from said first well into said second well, wherein conditions are provided in the second well for allowing the formation of a complex comprising the microbead, the analyte and the labeling reagent; and (e) identifying the presence or measuring the quantity of said analyte by detecting said labeling reagent contained in the complex using a measuring device with a detection beam set coaxially with the optical trapping means.

2. A method for performing a non-competitive immunoassay for detection of an analyte contained in a biological sample, comprising the steps of:

(a) providing a plurality of wells;

(b) providing a microbead coated with an anti-analyte reagent that recognizes and binds to the analyte;

(c) providing a labeling reagent that recognizes and binds to the analyte;

(d) loading the microbead into a first well, loading the biological sample into a second well, loading the labeling reagent into a third well, and loading buffer into a fourth well, wherein each well is connected to at least one other well by a microchannel, and wherein said microchannel is impermeable to the passive diffusion of the microbead, the biological sample, the labeling reagents and the buffer contained in said wells;

(e) transferring, by optical trapping means, the microbead from said first well into said second well through the microchannel connecting the first and the second wells, wherein conditions are provided in the second well for allowing the formation of a complex comprising the microbead and the analyte, if the analyte is present in the biological sample;

(f) transferring, by optical trapping means, the microbead/analyte complex from said second well into said third well, through the microchannel connecting the second and the third wells, wherein conditions are provided in the third well for further allowing the formation of a complex between the labeling reagent and the microbead-analyte complex from the second well;

(g) transferring, by optical trapping means, said second complex from said third well into said fourth well, through the microchannel connecting the third and the fourth wells; and (h) measuring the quantity of said labeling reagent bound to the analyte in the complex to determine the concentration of the analyte.

3. The method of claim 2 wherein said optical trapping means is comprised of a laser beam emitted from a laser source.

4. The method of claim 2 wherein said microbeads are between about 0.1 and about 50 μm in diameter.

5. The method of claim 2 wherein said microbeads are made from a material selected from the group consisting of glass, polyvinyl chloride, polystyrene, and dielectric materials.

6. The method of claim 2 wherein said measuring step is performed by fluorescence or luminescence detection.

7. The method of claim 2 wherein said transferring steps are performed by fixing the microbead in place by said optical trapping means and simultaneously moving said wells.

8. The method of claim 3, wherein said laser beam has an emission band near infrared wavelength.

9. The method of claim 8, wherein said wavelength is above 650 nm.

10. The method of claim 8, wherein said laser beam is emitted by neodymium:yttrium-aluminum-garnet (Nd:YAG) laser.

11. A method for performing a competitive immunoassay for detection of an analyte contained in a biological sample, comprising the steps of (a) providing a plurality of wells;

(b) providing a microbead coated with an anti-analyte reagent that recognizes and binds to the analyte and to a labeled analyte;

(c) providing a labeling reagent that recognizes and binds to the analyte;

(d) loading the microbead into a first well, loading the biological sample and the labeled analyte into a second well, and loading buffer into a third well, wherein each well is connected to at least one other well by a microchannel, and wherein said microchannel is impermeable to the passive diffusion of the microbead, the biological sample, the labeling reagents and the buffer contained in said wells;

(e) transferring, by optical trapping means, the microbead from said first well into said second well through the microchannel connecting the first and the second wells, wherein conditions are provided in the second well for allowing the labeled analyte to compete with the analyte for binding to said microbead and to form a complex comprising the labeled analyte and the microbead;

(f) transferring, by optical trapping means, said complex from said second well into said third well, through a microchannel connecting the second and the third wells; and (g) measuring the quantity of the labeled analyte bound to the microbead in the complex to determine the concentration of the analyte.

12. The method of claim 11, wherein said optical trapping means is comprised of a laser beam emitted from a laser source.

13. The method of claim 11 wherein said microbeads are between about 0.1 and about 50 $\mu$m in diameter.

14. The method of claim 13 wherein said microbeads are made from a material selected from the group consisting of glass, polyvinyl chloride, polystyrene, and dielectric materials.

15. The method of claim 11 wherein said measuring step is performed by fluorescence detection.

16. The method of claim 11 wherein said transferring steps are performed by fixing the microbead in place by said optical trapping means and simultaneously moving said wells.

* * * * *